US010335354B2

(12) United States Patent
Gracioso et al.

(10) Patent No.: US 10,335,354 B2
(45) Date of Patent: Jul. 2, 2019

(54) **TOPICAL COSMETIC TREATMENT OF SKIN AND SCALP AND CORRESPONDING ACTIVE INGREDIENT BASED ON AN EXTRACT OF *APIUM GRAVEOLENS***

(71) Applicant: SEDERMA, Le-Perray-en-Yvelines (FR)

(72) Inventors: Olga Gracioso, Courbevoie (FR); Caroline Ringenbach, Rambouillet (FR); Thibault Marchand, Neauphle le Vieux (FR); Philippe Mondon, Montrouge (FR); Nicolas Barriere, Ville d'Avray (FR)

(73) Assignee: SEDERMA, Le-Perray-en-Yvelines (FR)

( * ) Notice: Subject to any disclaimer, the term of this patent is extended or adjusted under 35 U.S.C. 154(b) by 0 days.

(21) Appl. No.: 15/560,738

(22) PCT Filed: Mar. 29, 2016

(86) PCT No.: PCT/IB2016/051760
§ 371 (c)(1),
(2) Date: Sep. 22, 2017

(87) PCT Pub. No.: WO2016/157073
PCT Pub. Date: Oct. 6, 2016

(65) Prior Publication Data
US 2018/0078481 A1 Mar. 22, 2018

(30) Foreign Application Priority Data
Mar. 30, 2015 (FR) ...................................... 15 52692

(51) Int. Cl.
*A61K 36/00* (2006.01)
*A61K 8/49* (2006.01)
*A61Q 19/00* (2006.01)
*A61K 8/9789* (2017.01)
*A61Q 5/00* (2006.01)
*A61Q 19/08* (2006.01)

(52) U.S. Cl.
CPC .......... *A61K 8/4973* (2013.01); *A61K 8/9789* (2017.08); *A61Q 5/006* (2013.01); *A61Q 19/00* (2013.01); *A61Q 19/08* (2013.01); *A61K 2800/5922* (2013.01)

(58) Field of Classification Search
CPC ..................................................... A61K 36/00
See application file for complete search history.

(56) References Cited

U.S. PATENT DOCUMENTS

| 6,203,782 | B1 | 3/2001 | Eliaz et al. | |
|---|---|---|---|---|
| 7,182,963 | B2 | 2/2007 | Lintner | |
| 2006/0165619 | A1 | 7/2006 | Lee et al. | |
| 2009/0098217 | A1 | 4/2009 | Blaszkowski | |
| 2010/0184852 | A1* | 7/2010 | De Saizieu | .......... A61K 31/343 514/470 |
| 2015/0150770 | A1 | 6/2015 | Morariu | |

FOREIGN PATENT DOCUMENTS

| CN | 103183654 | A | 7/2013 |
|---|---|---|---|
| FR | 2827509 | A1 | 1/2003 |
| FR | 2982150 | A1 | 5/2013 |
| GB | 2182943 | A | 5/1987 |
| JP | 0469314 | A | 3/1992 |
| JP | 08188528 | A | 7/1996 |
| JP | 2006036682 | A | 2/2006 |
| KR | 20130030491 | A | 3/2013 |
| WO | 0058347 | A1 | 10/2000 |
| WO | 03028692 | A2 | 4/2003 |
| WO | 2007029187 | A2 | 3/2007 |
| WO | 2014080376 | A2 | 5/2014 |
| WO | 2015181688 | A1 | 12/2015 |

OTHER PUBLICATIONS

Baananou et al, Antiulcerogenic activity of Apium graveolens seeds oils isolated by supercritical CO2. African Journal of Pharmacy and Pharmacology (2012), vol. 6, No. 10, pp. 756-762 (Year: 2012).*
International Search Report and Written Opinion for International Application No. PCT/IB2016/051760, dated Jun. 22, 2016—11 Pages.
Mintel, "Firming Whipped Body Cream", XP002766291, Database Accession No. 102929, Jul. 2001, 2 pages.
Mintel, "Naturally Enriching Hand & Nail Cream", XP002766494, Database Accession No. 1937059, Dec. 2012, 4 pages.
Lund, "Thin Layer and High Pressure Liquid Chromatographic Analysis of Celery Seed Oil", Journal of the Association of Official Analytical Chemists, vol. 61, No. 5, 1978, pp. 1083-1088.
International Search Report and Written Opinion for International Application No. PCT/EP2017/074265, dated Nov. 30, 2017, 14 pages.
International Search Report and Written Opinion for International Application No. PCT/US2017/074262, dated Jan. 3, 2018, 13 pages.

* cited by examiner

*Primary Examiner* — Qiuwen Mi
(74) *Attorney, Agent, or Firm* — RatnerPrestia

(57) ABSTRACT

The invention provides the use of at least one alkyl-phthalide or a plant extract comprising mainly said alkyl-phthalide for the topical cosmetic treatment of the skin and of the scalp, in particular an anti-dandruff treatment. According to the invention, a $CO_2$ supercritical extract of *Apium graveolens* seeds consisting mainly of sedanenolide may be used.

11 Claims, No Drawings
Specification includes a Sequence Listing.

TOPICAL COSMETIC TREATMENT OF SKIN AND SCALP AND CORRESPONDING ACTIVE INGREDIENT BASED ON AN EXTRACT OF *APIUM GRAVEOLENS*

This application is the U.S. National Phase application of PCT International Application No. PCT/IB2016/051760, filed Mar. 29, 2016, which claims the benefit of priority of French Patent Application No. FR 1552692, filed Mar. 30, 2015, the contents of which are incorporated herein by reference in their entirety for all purposes.

TECHNICAL FIELD

The present invention relates to a novel topical cosmetic treatment of the skin and scalp and a cosmetic active ingredient for said treatment based on an extract of *Apium graveolens*.

Cosmetics, hygiene and personal care, and dermo-pharmacy industries are concerned.

BACKGROUND ART

One of the challenges of cosmetics is to fight strongly against dandruff, often a benign condition of the scalp, but aesthetically unpleasant. This condition is characterized by the presence of dead cells or whitish scales on the scalp, in hair and on clothing, often accompanied by itching.

The origin of dandruff is related to the disturbance of one or several factors. As such, the increased production of sebum, which begins in adolescence, is an important factor although not sufficient. This sebum serves as substrate for yeast of *Malassezia* type, said yeast multiplying themself and producing irritating lipids disrupting the balance (homeostasis) of the scalp. Having sebum, yeast or a dry scalp is not enough to have dandruff. Individual susceptibility and external factors play an important role also. Among these are found in particular: hair treatments that are too aggressive, extreme weather conditions, poor diet, fatigue, stress or pollution.

Two types of dandruff can be distinguished. In the dry form of dandruff, scalp seems to be too dry, the amount of dandruff is often low to moderate; scales are small and isolated. Mild itching is often, although scalp is not red. This condition can evolve into a form represented by oily dandruff although the latter may appear immediately associated with an abundant production of sebum. Scales are thicker, larger and associated with each other to form fatty, wet and yellowish plaques. Thereafter the scalp has often inflammatory changes, with more or less spreading redness, irritating condition and itching.

The present invention aims in particular to provide a means for preventing or treating unsightly dandruff and signs that accompany them such an oily and shiny skin, irritation and itching.

The *Apium graveolens* plant, commonly called celery, is part of the family of Apiaceae or Umbelliferae family, which includes many other edible plants such as carrot and coriander. This plant is not toxic; all parts of it can be consumed as raw or cooked vegetables. The seeds are also used as spices.

Italy is the country of origin, this plant being widespread in the world, especially in Europe, Egypt, Algeria, Ethiopia, Asia and India.

Celery seeds contain about 3% of volatile oil and 15% of non-volatile vegetable oil.

An essential oil extracted from celery seeds comprises terpenes (D-limonene>60% and selinene 10-20%) and phthalides (1-4%). Among the predominant phthalides, there is the 3-n-butyl-phthalide, the sedanolide and sedanenolide (also called senkyunenolide A).

The nonvolatile part includes petroselinic, oleic, linoleic, myristic, palmitic, palmitoleic, stearic and myristoleic fatty acids.

The *Apium graveolens* therefore comprises potentially very many active compounds. As a medicinal plant, it is recommended for thousands of years for many properties: aphrodisiac, anthelmintic, antispasmodic, anti-inflammatory, carminative, diuretic, emmenagogue, laxative, sedative, stimulant and tonic. The plant can be used against asthma, bronchitis and rheumatism. The wild celery seeds are used in traditional medicine in India and other countries that have adopted the Ayurvedic traditions to heal, as a tranquilizer, antispasmodic, nerve tonic, diuretic and anti-rheumatic. The phthalides included in the *Apium graveolens* are described as active against cancer, high blood pressure and cholesterol. The world of living organisms and plants in particular represents a very important source of innovative active molecules for cosmetics and pharmaceuticals. To extract and concentrate them, there are different methods, and the composition of the obtained extract will obviously depend on the method and the operating conditions.

The extraction technique with supercritical $CO_2$ is already widely used in the food, pharmaceutical and perfumery industries. Gaseous $CO_2$, present in low concentrations in the air, is compressed so that it becomes liquid. It is then an excellent solvent for fat-soluble molecules. Inert, it reacts little with the extracted molecules and leaves no residue since it is evaporated at the end of process and captured to be reused.

An essential oil of celery, obtained by hydro-distillation, comprising in majority D-limonene has been proposed in cosmetics to treat pigmentation spots.

SUMMARY OF THE INVENTION

The present invention provides the use of at least one alkyl-phthalide or a plant extract comprising said alkyl-phthalide as major compound, for the non-therapeutic cosmetic topical treatment of the skin or scalp.

"Cosmetic treatment" means a treatment that addresses a normal, healthy skin or scalp, said treatment being intended to improve the appearance and condition in order to beautify and/or reduce of any feelings of discomfort. Such treatment has no therapeutic aim.

"Alkyl-phthalide" encompasses according to the invention phthalides in which the 6-carbon ring is aromatic and hydro-phthalides in which the 6-carbon ring has only 1 or 2 unsaturated bonds.

An alkyl-phthalide according to the invention has therefore the following general formula I:

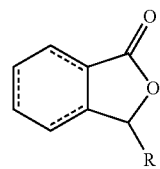

R being an alkyl chain of 1 to 8 carbon atoms, preferably 1 to 4, and preferably 4 (butyl phthalides), linear or branched, that can be substituted by an OH or amine function (secondary or tertiary).

The present invention encompasses pure alkyl-phthalides which can be obtained by chemical synthesis or by extraction and purification from a plant comprising them.

It also encompasses plant extracts, such as *Apium graveolens*, which are characterized in that they predominantly comprise at least one alkyl-phthalide as active compound.

In vitro and in vivo tests detailed thereafter in the description show the effects of the cosmetic treatment according to the invention, especially on the scalp, for preventing and/or treating dandruff conditions, to improve the mechanical properties of the dermal extracellular matrix (density, firmness, fine lines and wrinkles in particular) and to prevent and/or treat an oily skin.

Specifically, it has been shown that the cosmetic treatment according to the present invention is capable of acting at 5 levels on the scalp and/or skin:

The skin microflora;
The amount of sebum;
The skin barrier;
The cutaneous irritation/itching; and
The extracellular matrix of the dermis.

1) Regarding the Skin Microflora

Yeast of *Malassezia* type are present on almost every scalp at the level of the hair follicles. Their presence in itself is not a problem in many people without dandruff, but their proportion in the skin microflora is correlated with dandruff state.

They secrete specific phospholipases and lipases whose role is to extract energy from triglycerides of sebum or phospholipids. This in return forms lipidic byproducts, such as arachidonic acid or oleic acid, which can be irritating if present in too large amounts. In addition, some yeast belonging to the *Malassezia* genus, among which *Malassezia furfur* and *Malassezia globosa*, cause interleukin-8 formation by keratinocytes and induce hyperproliferation of these cells with as a consequence an alteration of the skin barrier function (stratum corneum), which promotes even more the negative action of the by-products of bacteria and yeast such as oleic or arachidonic acids and makes the scalp more sensitive. Improving the condition of the scalp thus requires control of the yeast of the *Malassezia* genus that can cause major disruptions.

In vitro and in vivo tests given below show that according to the invention, these microorganisms and dandruff are fight.

2) Regarding the Sebum Production

Sebum is a mixture of complex lipids (triglycerides, fatty acids, waxes, esterified sterols, cholesterol and derivatives, and squalene) produced by sebocytes. From a physiological point of view, sebum is intended to protect the skin by isolating it from the outside. It is clearly known now that it plays a role in the emergence of dandruff states. Indeed, the overproduction of sebum at puberty and incidence of dandruff states increase in parallel of one another. Moreover, dandruffs are seen only on areas rich in sebum.

As noticed above, these lipids are used as substrate for *Malassezia* yeast involved in dandruff states. Furthermore, as regard oily dandruff, a greater seborrhea accompanies overproduction of immature cells, glues and maintains these on the scalp and hair.

Regarding the so-called oily skins, too much sebum will give them a shiny appearance, clog and open the pores, cause bacterial growth and cause skin imperfections including redness.

It is therefore necessary either for dandruff or oily skin to reduce the production of lipids by the sebocytes producing sebum.

3) At the Level of the Cutaneous Barrier

Skin and scalp are epithelia that form the stratum corneum. They are renewed continuously by desquamation. This forms a very effective barrier with regard to external aggression and limits the water loss of the body. This barrier is an assembly of great complexity involving on one hand the cells having no nucleus, flat and strongly bonded together and, on the other hand, lipids whose composition and assembly provide the unique properties of this structure very resistant to physical, chemical and biological environmental aggressions.

In healthy skin, the stratum corneum is formed by the terminal maturation of viable underlying cells of the granular layer. Superficial viable cells of the epidermis, having a lipid contour, are transformed into little flat bricks coreless, the corneocytes, thanks in particular to proteins, such as involucrin, loricrin, filaggrin and SPRRs (small proline-rich region proteins), all linked together. The SPRRs operate as bridging agents strengthening the horny envelope and governing the toughness, strength and flexibility properties. Other proteins are expressed as the LCE3B (Late Cornified Envelope protein 3B) induced when it is necessary to repair the skin barrier. The corneocytes are strongly linked together by corneodesmosomes and "cemented" by organized layers of extracellular complex lipids: cholesterol, ceramides and neutral lipids.

An optimal skin barrier function ensures that, thanks to desquamation, skin and scalp eliminate their superficial cells in an insensitive and not visible manner. Desquamation is permitted by serine proteases, the KLK (Kallikrein-related peptidase), which break the ties of the corneocytes between each other's (corneodesmosomes), the SPINK5 (Serine Protease Inhibitor Kazal-type 5) regulating their activity. Loss of function of the SPINK5 causes hyper-peeling of immature cells and loss of homeostasis of the stratum corneum.

The loss of integrity of the skin barrier is often observed in dandruff states. The division of the cells of the basal layer of the epidermis becomes too fast. The cells that rise to the surface of the skin do not have time to finish their maturation and develop into small corneocyte. Instead, larger cell structures are formed and therefore more visible, having a core residual (dandruff). This abnormal acceleration of desquamation facilitates the penetration of molecules and external agents that can irritate the skin. This results in a disturbance of the protective and regulatory functions of the stratum in particular the antimicrobial function.

In vitro and in vivo tests given below in the description show that, according to the invention, the skin barrier is reinforced, by stimulating the synthesis of proteins and lipids thereof, as well as the functional proteins LCE3B and SPINK5.

4) At the Level of Itching and Irritation of Skin

The disturbance of the scalp and dandruff states caused by a deficient skin barrier, the presence of *Malassezia* genus yeast in large amounts and/or any excess of sebum induce at the end itching and irritation for the person. Red patches may even appear.

In vitro and in vivo tests given below in the description show that, according to the invention, skin itching and irritation are decreased.

5) At the Level of the Dermis Matrix

The loss of density and thickness of the dermis are in particular related to a reduction of the synthesis of collagen I by the dermal fibroblasts during cutaneous aging. Collagen I, being the most abundant protein of the dermal extracellular matrix, is essential for firm and less wrinkled skin.

As a complement of activity, it has been shown that the alkyl-phthalides, or an extract of *Apium graveolens* seeds comprising them, according to the invention has the property of stimulating the production of collagen in dermal fibroblasts.

More generally, the present invention thus provides the use of alkyl-phthalide(s) or a plant extract containing alkyl-phthalide(s) as major compound(s) for the following non-topical therapeutic cosmetic treatment(s):

Anti dandruff; and/or
Of irritation and/or itching of skin and scalp; and/or
To limit the production of sebum of skin and scalp; and/or Of oily skin and/or dilated pores; and/or To strengthen the skin barrier to restore skin homeostasis; and/or Anti-wrinkle and fine lines and to improve the mechanical properties of the skin (loss of density, and thus loss for example of firmness) through stimulation of collagen synthesis.

Most preferably according to the invention, used alkyl-phthalides comprise sedanenolide, sedanolide and/or 3-n-butylphthalide. These three alkyl-phthalides, shown thereafter, are those comprised in the volatile portion of the seeds of the *Apium graveolens* plant.

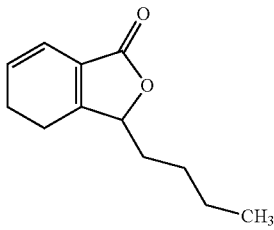

Sedanenolide = Senkyunolide A = 3-butyl-6,7-dihydrophthalide

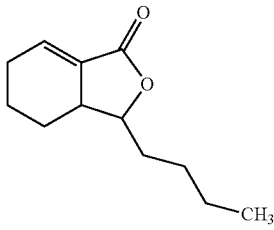

Sedanolide

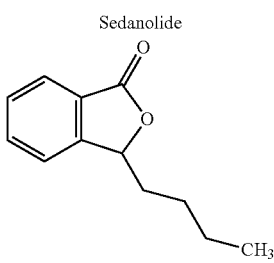

3-n-butylphthalide

Thus, according to a preferred feature of the invention, an extract of *Apium graveolens* seeds comprising sedanenolide, sedanolide and 3-n-butylphthalide is used according to the invention. Other plants may be used to extract one alkyl-phthalide according to the invention or produce an extract containing it predominantly, particularly preferably one of the 3 alkyl-phthalides present in the seeds of *Apium graveolens*.

And according to further preferred features according to the invention an extract prepared by $CO_2$ supercritical extraction is used which provides an extract comprising alkyl-phthalides as major compounds, preferably at least 50%, preferably at least 65%, the remaining compounds mainly consisting of terpenes and traces of fatty acids.

According to the invention the weight contents of these 3 phthalides based on total phthalides vary between:
Sedanolide: 0-45%
Sedanenolide: 45-90%
3-n-butylphthalide: 0-30%

Advantageously, an extract comprising preferably among the 3 alkyl-phthalides the sedanenolide as the major compound, preferably comprising at least 50%, and preferably at least 60%, and more preferably at least 70% of sedanenolide based on total phthalides, is used.

The extract may be prepared by $CO_2$ supercritical extraction in a pressure range of 75 to 300 bars and in a temperature range of 30° C. to 80° C. Preferably the extraction will be done under 90 bars pressure and at 40° C.

Other extraction methods can be used to obtain an extract according to the invention comprising a majority of at least one alkyl-phthalide, including extraction with a nonpolar solvent such as hexane.

The present invention also provides a cosmetic active ingredient comprising in a physiologically acceptable matrix an oily extract comprising mainly alkyl phthalides, said extract being obtainable by supercritical $CO_2$ extraction of *Apium graveolens* seeds, and a cosmetic composition comprising at least said active ingredient in a physiologically acceptable excipient.

DETAILED DESCRIPTION

The present invention will be better understood and other advantages will appear from the following detailed description of preparation examples and in vitro and in vivo tests.

Preparation of Compositions According to the Invention

A cosmetic composition, especially topical, comprises at least one alkyl-phthalide or a plant extract comprising in majority said at least one alkyl-phthalide in a physiologically acceptable medium. According to the excipient and the alkyl-phthalide dosage, this composition will be a concentrated active ingredient or a final composition less concentrated directly for the end user.

"Physiologically acceptable medium" means according to the present invention, without limitation, an aqueous or hydro-alcoholic solution, a water-in-oil emulsion, an oil-in-water emulsion, a micro-emulsion, an aqueous gel, an anhydrous gel, a serum, a dispersion of vesicles, or a powder.

"Physiologically acceptable" means that the compositions are suitable for topical or transdermal use, in contact with mucous membranes, appendages (nails, hairs), scalp and skin of mammals, particularly human, compositions which may be ingested, or injected into the skin, without risk of toxicity, incompatibility, instability, allergic response, and others.

This "physiologically acceptable medium" forms what is commonly called the excipient of the composition.

The alkyl-phthalide(s) or plant extract comprising such may be combined with other active ingredients at effective concentrations that can act synergistically or additionally for reinforcing and achieving the desired effects described for the invention, such as the following agents: UVA and/or UVB radiation filtering agents, hydrating, moisturizing, humectant, calming, dermo-relaxing, slimming, restructuring, firming, replumping, lifting, antidandruff, smoothing, acting on blood microcirculation, inflammation, free radicals, anti-aging, anti-fine lines and wrinkles, lightening, acting on complexion, anti-glycation, anti-carbonylation, pro-pigmenting, acting on stratum corneum, on dermal-epidermal junction, on HSP protein production, on firmness, elasticity and tone of skin, on hair growth or anti-regrowth (including eyelashes and eyebrows), on eye contours (dark circles and under eye bags), peptides, vitamins, etc.

For a scalp treatment in addition to or reinforcement of activity is preferably used:

An anti-dandruff active acting as antifungal: such as zinc pyrithione, ketoconazole, climbazole, piroctone olamine or selenium disulphide;

A moisturizing agent such as DuraQuench™ (Croda);

An active rebalancing the skin microflora as HAIRSPA™ (Sederma);

A calming active as PACIFEEL™ (Sederma); and/or

An antibacterial, moisturizing and anti-stinging active as OSMOCIDE™ (Sederma); and/or A detoxification and skin reinforcement against air pollutants active as CITYSTEM™ (Sederma); and/or A cosmetic active to prevent hair loss and stimulate their growth as CAPIGENE™, CAPILECTINE™, PROCAPIL™ (Sederma); or to reinforce the structure of damaged hair as CERAMIDE A2™, HELIOGENOL™ (Sederma); or to smooth the hair as FRUIT BIO™ (Sederma).

The treatment of the invention may be applied to all body parts, and more specifically according to the preconized indication to the face, body, neckline or scalp, in whatever form or carrier known to those skilled in the art, in particular in the form of solution, dispersion, emulsion, paste, or powder, individually or as a premix or in vehicles individually or as a premix in vectors such as macro-, micro- or nano-capsules, macro-, micro- or, nano-spheres, liposomes, oleosomes or chylomicrons, macro-, micro-, or nanoparticles or macro-, micro- or nano-sponges, micro- or nano-emulsions or adsorbed on organic polymer powders, talcs, bentonites, spores or exines, and other inorganic or organic supports. In cosmetics in particular, applications can be offered in skincare ranges for the face, body and scalp. In general, the alkyl-phthalide(s) or plant extract(s) according to the invention may be used in any form, in a form bound to or incorporated in or absorbed in or adsorbed on macro-, micro-, and nanoparticles, or macro-, micro-, and nano-capsules, for the treatment of textiles, natural or synthetic fibres, wools, and any materials that may be used for clothing or underwear for day or night intended to come into contact with the skin, handkerchiefs or cloths, to exert their cosmetic effect via this skin/textile contact and to allow continuous topical delivery.

The CTFA («International Cosmetic Ingredient Dictionary & Handbook» (16th Ed. 2016) published by «the Personal Care Products council», ex-«the Cosmetic, Toiletry, and Fragrance Association, Inc.», Washington, D.C.), describes a non-limited wide variety of cosmetic and pharmaceutical ingredients commonly used in the skin care industry, which are suitable for use as additional ingredients in the compositions according to the present invention.

Further additional skin care actives that are particularly useful can be found in the commercial literature of Sederma and on the website www.sederma.com.

The following commercial actives can also be mentioned, as examples: betaine, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Argireline™ (commercial name for the acetyl hexapeptide-3 of Lipotec), spilanthol or an extract of *Acmella oleracea* known under the commercial name Gatuline Expression™, an extract of *Boswellia serrata* known under the commercial name Boswellin™, Deepaline PVB™ (Seppic), Syn-AKE™ (Pentapharm), Ameliox™, Bioxilift™ (Silab), PhytoCellTec™ Argan (Mibelle), Papilactyl D™ (Silab), Preventhelia™ (Lipotec), and from Sederma: Subliskin™, Venuceane™, Moist 24™, Vegesome Moist 24™, Essenskin™, Juvinity™, Revidrat™, Resistem™, Chronodyn™, Kombuchka™, Chromocare™, Calmosensine™, Glycokin factor S™ Biobustyl™, Idealift™, Ceramide 2™, Ceramide A2™ et Ceramide HO3™, Legance™, Intenslim™, Prodizia™, Beautifeye™, Pacifeel™, NG-shea butter unsaponifiables (natural grade), Zingerslim™, Meiritage™, Senestem™, Sebuless™, Majestem™, Rubistem™, Citystem™, or mixture thereof.

Among other plant extracts which can be combined with the alkyl phthalide(s) or plant extract(s) of the invention, there may more particularly be mentioned extracts of Ivy, in particular English Ivy (*Hedera helix*), of *Bupleurum chinensis*, of *Bupleurum falcatum*, of *arnica* (*Arnica montana* L), of rosemary (*Rosmarinus officinalis* N), of marigold (*Calendula officinalis*), of sage (*Salvia officinalis* L), of ginseng (*Panax ginseng*), of ginko *biloba*, of St.-John's-Wort (*Hyperycum perforatum*), of butcher's-broom (*Ruscus aculeates* L), of European meadowsweet (*Filipendula ulmaria* L), of big-flowered Jarva tea (*Orthosiphon staminicus* benth), of artichoke (*Cynara scolymus*), of algae (*Fucus vesiculosus*), of birch (*Betula alba*), of green tea, of *cola* nuts (*Cola nipida*), of horse-chestnut, of bamboo, of *Centella asiatica*, of heather, of *fucus*, of willow, of mouse-ear, of escine, of cangzhu, of chrysanthellum indicum, of the plants of the *Armeniacea* genus, *Atractylodis platicodon, Sinnomenum, Pharbitidis, Flemingia*, of *Coleus* such as *C. Forskohlii, C. blumei, C. esquirolii, C. scutellaroides, C. xanthantus* and *C. Barbatus*, such as the extract of root of *Coleus barbatus*, extracts of *Ballote*, of *Guioa*, of *Davallia*, of *Terminalia*, of *Barringtonia*, of *Trema*, of *antirobia*, *cecropia*, *argania*, *dioscoreae* such as *Dioscorea opposita* or Mexican, extracts of *Ammi visnaga*, of *Siegesbeckia*, in particular *Siegesbeckia orientalis*, vegetable extracts of the family of Ericaceae, in particular bilberry extracts (*Vaccinium angustifollium*) or *Arctostaphylos uva ursi*, aloe vera, plant containing sterols (e.g., phytosterol), Manjistha (extracted from plants of the genus *Rubia*, particularly *Rubia cordifolia*), and Guggal (extracted from plants of the genus *Commiphora*, particularly *Commiphora mukul*), kola extract, chamomile, red clover extract, *Piper methysticum* extract (Kava Kava™ from Sederma), *Bacopa monieri* extract (Bacocalmine™ from Sederma) and sea whip extract, extracts of *Glycyrrhiza glabra*, of mulberry, of *melaleuca* (tea tree), of *Larrea divaricata*, of *Rabdosia rubescens*, of *Euglena gracilis*, of *Fibraurea recisa Hirudinea*, of *Chaparral sorghum*, of sun flower extract, of *Enantia chlorantha*, of Mitracarpe of *Spermacocea* genus, of *Buchu barosma*, of *Lawsonia inermis* L., of *Adiantium capillus-veneris* L., of *Chelidonium majus*, of *Luffa cylindrica*, of Japanese Mandarin (*Citrus reticulata Blanco* var. *unshiu*), of *Camelia sinensis*, of *Imperata cylindrica*, of *Glaucium flavum*, of *Cupressus sempervirens*, of *Polygonatum multiflorum*, of *loveyly hemsleya*, of *Sambucus nigra*, of *Phaseolus lunatus*, of *Centaurium*, of *Macrocystis pyrifera*, of *Turnera diffusa*, of *Anemarrhena asphodeloides*, of *Portulaca pilosa*, of *Humulus lupulus*, of *Coffea arabica*, of *Ilex paraguariensis*, or of *Globularia cordifolia*, of *Albizzia julibrissin*, of *Oxydendron arboretum*, of *Zingimber zerumbet* smith, of *Astragalus membranaceus*, of *Atractylodes macrocephalae*, of *Plantago lanceolata*, of *Leontopodium alpinism*, of *Mirabilis jalapa*, of *Marrubium vulgare*, or of orchids.

The compositions of the present invention may include one or more peptides, including, without limitation, di-, tri-, tetra-, penta- and hexapeptides and their derivatives. According to a particular embodiment, the concentration of the additional peptide, in the composition, ranges from $1 \times 10^{-7}\%$ and 20%, preferably from $1 \times 10^{-6}\%$ and 10%, preferably between $1 \times 10^{-5}\%$ and 5% by weight.

According to the present invention, the term "peptide" refers to peptides containing 10 amino acids or less, their derivatives, isomers and complexes with other species such as a metal ion (e.g. copper, zinc, manganese, magnesium, and others). The term "peptides" refers to both natural peptides and synthetic peptides. It also refers to compositions that contain peptides and which are found in nature, and/or are commercially available.

Suitable dipeptides for use herein include but are not limited to Carnosine (βAH), YR, VW, NF, DF, KT, KC, CK, KP, KK, TT, PA, PM or PP.

Suitable tripeptides for use herein include, but are not limited to RKR, HGG, GKH, GGH, GHG, KFK, KAvaK, KPAK, KAbuK, KAcaK, KPK, KMOK, KMO$_2$K (MO$_2$ being a di-oxygenated sulfoxide methionine), KVK, PPL, PPR, SPR, QPA, LPA or SPA.

Suitable tetrapeptides for use herein include but are not limited to RSRK (SEQ ID NO: 1), GQPR (SEQ ID NO: 2), KTFK (SEQ ID NO: 3), KTAK (SEQ ID NO: 4), KAYK (SEQ ID NO: 5) or KFYK (SEQ ID NO: 6).

Suitable pentapeptides include, but are not limited to KTTKS (SEQ ID NO: 7). Suitable hexapeptides include but are not limited to GKTTKS (SEQ ID NO: 8) and VGVAPG (SEQ ID NO: 9).

Other suitable peptides for use herein include, but are not limited to: lipophilic derivatives of peptides, preferably palmitoyl (Pal) derivatives, and metal complexes as aforementioned (e.g. copper complex of the tripeptide HGG). Preferred dipeptide include for example N-Palmitoyl-β-Ala-His, N-Acetyl-Tyr-Arg-hexadecylester (Calmosensine™, Idealift™ from Sederma), Pal-RT or Pal-KT (Sederma). Preferred tripeptide derivatives include for example Pal-GKH and Pal-GHK (from Sederma), the copper derivative of HGG (Lamin™ from Sigma), Lipospondin (N-Elaidoyl-KFK) and its analogs of conservative substitution, N-Acetyl-RKR-NH$_2$ (Peptide CK+), N-Biot-GHK (from Sederma), Pal-KAvaK, Pal-KβAlaK, Pal-KAbuK, Pal-KAcaK, or Pal-KMO$_2$K (Matrixyl® synthe'6® from Sederma), PalKVK (Syn-Coll™ of DSM), and derivatives thereof.

Here can also be cited the anti-aging tripeptides of general formula X-Pro*-Pro*-Xaa-Y disclosed in WO2015181688 with Xaa selected from Leu, Arg, Lys, Ala, Ser, and Asp; at the N terminal end, X selected from H, —CO—R$_1$ and —SO$_2$—R$_1$ and at the C terminal end Y selected from OH, OR$_1$, NH$_2$, NHR$_1$ or NR$_1$R$_2$; R$_1$ and R$_2$ being, independently from each other, selected from an alkyl, aryl, aralkyl, alkylaryl, alkoxy et aryloxy group, that can be linear, branched, cyclic polycyclic, saturated, unsaturated, hydroxylated, carbonylated, phosphorylated and/or sulfured, said group having or not an O, S and/or N heteroatom in its skeleton and Pro* corresponding to a Proline, analog or derivative thereof; comprising for example Myr-PPL-OH and Myr-PPR-OH.

Here can further be cited also the propigmenting and/or pro-mec dipeptides and tripeptides of general formula X-(Xaa$_1$)n-Pro*-Xaa$_2$-Y disclosed in WO2014/080376, with n=0, 1 or 2, Xaa$_1$ an hydrophobic aminoacid selected from Ala, Val, Met, Leu, Iso, Phe, Pro, and analogs and derivatives thereof; or a polar aminoacid selected from Ser, Thr, Tyr, Asp, Glu and analogs and derivatives thereof; and when n=2 the two aminoacids Xaa$_1$ being the same or different; Xaa$_2$ being an hydrophobic aminoacid selected from Ala, Val, Met, Leu, Iso, Phe, and analogs and derivatives thereof, or a basic aminoacid selected from Arg, Lys, His, and analogs and derivatives thereof; at the N terminal end X being selected from H, —CO—R$_1$ and —SO$_2$—R$_1$; at the C terminal end Y being selected from OH, OR$_1$, NH$_2$, NHR$_1$ or NR$_1$R$_2$; R$_1$ and R$_2$ being, independently from each other, selected from an alkyl, aryl, aralkyl, alkylaryl, alkoxy et aryloxy group, that can be linear, branched, cyclic polycyclic, saturated, unsaturated, hydroxylated, carbonylated, phosphorylated and/or sulfured, said group having or not an O, S and/or N heteroatom in its skeleton and Pro* corresponding to a Proline, analog or derivative thereof; comprising for example the following peptides Pal-SPR-OH, Pal-PPR-OH, Pal-QPA-OH, Pal-LPAOH, Myr-SPA-OH, Pal-PM-OH, Pal-PA-OH and Pal-PP-OH.

Suitable tetrapeptide derivatives for use according to the present invention include, but are not limited to, Pal-GQPR (SEQ ID NO: 10) (from Sederma) and Pal-KTFK (SEQ ID NO: 11) or Ela-KTFK (SEQ ID NO: 12), Ela-KTAK (SEQ ID NO: 13), Ela-KAYK (SEQ ID NO: 14) or Ela-KFYK (SEQ ID NO: 15). Suitable pentapeptide derivatives for use herein include, but are not limited to, Pal-KTTKS (SEQ ID NO: 16) (available as Matrixyl® from Sederma), Pal-YG-GFXaa (SEQ ID NO: 17) with Xaa being Leu or Pro, or mixtures thereof. Suitable hexapeptide derivatives for use herein include, but are not limited to, Pal-VGVAPG (SEQ ID NO: 18), Pal-GKTTKS (SEQ ID NO: 19), Pal-HLDI-IXaa with Xaa being Trp, Phe, Tyr, Tic, 7-hydroxy-Tic ou Tpi (SEQ ID NO: 20) and derivatives thereof. The mixture of Pal-GHK and Pal-GQPR (SEQ ID NO: 10) (Matrixyl® 3000, Sederma) can also be mentioned.

The preferred compositions commercially available containing a tripeptide or a derivative include Biopeptide-CL™, Maxilip™, Biobustyl™, Procapil™ and Matrixyl® synthe'6® of Sederma. The compositions commercially available preferred sources of tetrapeptides include Rigin™, Eyeliss™, Matrixyl® Reloaded and Matrixyl 3000® which contain between 50 and 500 ppm of Pal-GQPR (SEQ ID NO: 10) and an excipient, proposed by Sederma.

The following marketed peptides can be mentioned as well as additional active ingredients:

Vialox™ (INCI name=Pentapeptide-3 (synthetic peptide comprising alanine, arginine, isoleucine, glycine and proline)), Syn-ake™ (β-Ala-Pro-Dab-NH-Bzl) or Syn-Coll™ (Pal-Lys-Val-Lys-OH) marketed by Pentapharm;

Argireline™ (Ac-Glu-Glu-Met-Gln-Arg-Arg-NH$_2$ (INCI name=Acetyl hexapeptide-3) (SEQ ID NO: 21), Leuphasyl™ (Tyr-D-Ala-Gly-Phe-Leu) (SEQ ID NO: 22), Aldenine™ (Gly-His-Lys), Trylagen™ (INCI name=*Pseudoalteromonas* Ferment Extract, Hydro lyzed Wheat Protein, Hydro lyzed Soy Protein, Tripeptide-10 Citrulline (reaction product of Citrulline and Tripeptide-10 (synthetic peptide constituted of aspartic acid, isoleucine and lysine)), Tripeptide-1), Eyeseryl™ (Ac-β-Ala-His-Ser-His)(SEQ ID NO: 23), Serilesine™ (Ser-Ile-Lys-Val-Ala-Val) (SEQ ID NO 24) or Decorinyl™ (INCI name: Tripeptide-10 Citrulline=reaction product of Citrulline and Tripeptide-10 (synthetic peptide constituted of aspartic acid, isoleucine and lysine) marketed by Lipotec;

Collaxyl™ (Gly-Pro-Gln-Gly-Pro-Gln (SEQ ID NO 25)) or Quintescine™ (Cys-Gly) marketed by Vincience;

Cytokinol™ LS (casein hydrolysate) marketed by Les Laboratoires Serobiologiques/Cognis;

Kollaren™ (Gly-His-Lys), IP2000™ (Pal-Val-Tyr-Val) or Meliprene™ (INCI name=Monofluoroheptapeptide-1: reaction product of acetic acide and a synthetic peptide comprising arginine, glycine, glutamic acid, histidine, norleucine, p-fluorophenylalanine and tryptophan) marketed by l'Institut Européen de Biologie Cellulaire;

Neutrazen™ (Pal-His-D-Phe-Arg-NH$_2$) marketed by Innovations; or

BONT-L-Peptide™ (INCI name=Palmitoyl Hexapeptide-19: reaction product of palmitic acid and Hexapeptide-19 (synthetic peptide constituted of asparagine, aspartic acid, lysine and methionine), Timp-Peptide™ (INCI name=Acetyl Hexapeptide-20: reaction product obtained by acetylation of Hexapeptide-20 (synthetic peptide constituted of alanine, glycine, lysine, valine and proline) or ECM Moduline™ (INCI name=Palmitoyl Tripeptide-28: reaction product of palmitic acid and Tripeptide-28 (synthetic peptide constituted of arginine, lysine and phenylalanine) marketed by Infinitec Activos.

More specifically, according to the invention the alkylphthalide(s) or plant extract comprising such may be combined with at least one of compounds selected from compounds of the vitamin B3, compounds such as niacinamide or tocopherol, retinoid compounds such as retinol, hexamidine, α-lipoic acid, resveratrol or DHEA, hyaluronic acid, peptides, in particular N-acetyl-Tyr-Arg-O-hexadecyl ester, Pal-VGVAPG (SEQ ID NO: 18), Pal-KTTKS (SEQ ID NO: 16), Pal-GHK, Pal-KMO$_2$K and Pal-GQPR (SEQ ID NO: 10), which are widely used active ingredients in topical cosmetic or dermopharmaceutical compositions.

The present invention also provides a method of cosmetic or dermatological topical treatment for improving the appearance and condition of the skin and scalp, comprising the topical application to the skin of a subject in need thereof an effective amount of at least one alkyl-phthalide or a plant extract comprising in majority said alkyl-phthalide or a composition comprising them, in a physiologically acceptable excipient.

"Topical treatment" or "topical use" means according to the invention, an application that is intended to act where it is applied: skin and/or scalp.

A composition according to the invention may be applied locally to targeted areas, for example using a cannula type of applicator suitable for the scalp.

The "effective" amount depends on various factors, such as the age, the condition of the patient, the seriousness of the disorder or pathology, the administration mode, etc. An effective amount means a non-toxic amount enough to achieve the desired effect.

All percentages and ratios used herein are by weight of the total composition and all measurements are made at 25° C. unless it is otherwise specified.

For example, for a cosmetic treatment of the face, the European Cosmetics Directive has set a standard amount for applying a cream of 2.72 mg/cm$^2$/day/person and for a body lotion of 0.5 mg/cm$^2$/day/person.

For example, for a scalp hair treatment, a dose of total phthalides from 0.5 to 2 mg is recommended to apply per week for at least 1 week, preferably at least 3 weeks. For example according to a treatment of at least 3 times per week, applying a dose of 10 grams of shampoo, and then 10 grams of a non-rinsed after-shampoo lotion ("Leave-on") with respectively 2% (shampoo) and 3% ("Leave-on") of the active ingredient containing the extract according to the invention (according to formulas 1.1 and 1.2 of the § D Galenics data below).

According to other specific features, the cosmetic treatment method according to the invention can be combined with one or more other treatment methods targeting the skin such as lumino-therapy, heat or aromatherapy treatments.

According to the invention, devices with several compartments or kits may be proposed to apply the method described above which may include for example and non-restrictively, a first compartment containing a composition comprising at least one alkyl-phthalide or a plant extract comprising it as the major compound according to the invention, and in a second compartment another active ingredient and/or excipient, the compositions contained in the said first and second compartments in this case being considered to be a combination composition for simultaneous, separate or stepwise use in time, particularly in one of the treatment methods recited above.

The treatment method according to the invention is more particularly suitable for a cosmetic treatment of the scalp, and in particular of dandruff states, oily skins (treatment of the gloss and/or dilated pores) of lines and wrinkles and loss of mechanical properties of the skin (loss of firmness in particular).

A) Example of Preparation of an *Apium graveolens* Seeds Extract that can be Used in the Context of the Invention The *Apium graveolens* seeds are ground to a particle size of powder around 800 µm. This powder is then extracted with supercritical CO$_2$ under 90 bars pressure and at 40° C. The residual water that may be present in the final extract is then removed if necessary (for example by decantation, vacuum evaporation, lyophilization). The extraction yield is around 2.5%. The extract is in the form of an oily liquid, clear to slightly opalescent, colorless to pale yellow.

The resulting extract is passed on Ultra High Performance Liquid Chromatography (UHPLC) on a C18 column with as mobile phase a water/acetonitrile gradient, to dose the various phthalides.

This analysis confirms the presence of 71% of total phthalides in the extract comprising the 3-alkyl phthalides: 10% of 3-n-butylphthalide, 30% of sedanolide and 60% of sedanenolide by weight relative to the total phthalides. The extract can be used pure or diluted.

B) Formulation of an Active Ingredient that can be Used in the Context of the Invention The active ingredient is a composition comprising the extract of *Apium graveolens* seeds obtained according to A) above dissolved in a matrix forming a physiologically acceptable medium. This active ingredient is particularly intended for the cosmetics industry for the preparation of cosmetics, creams, gels, etc. (See galenic examples at point D) below).

An extract obtained according to A) above can be diluted in any physiologically acceptable fatty excipient to reach at the end a concentration of 500 ppm of alkyl-phthalides. Esterified oil is preferably used of Caprylic/Capric Triglyceride type for this dilution.

For example, and for the description of the in vivo tests and the galenic of point D) below, it is this dilution that has been preferably used. This constitutes the active ingredient that will used itself preferably at between 1 and 5% in a cosmetic composition that can be applied on the skin.

C) In Vitro Test Results

In vitro tests were carried out from a crude extract of seed oil of *Apium graveolens* manufactured according to the production method described in A) above. In general, 8, 16 and 24 ppm of this extract, respectively corresponding to 5, 10 and 15 ppm of total phthalides, were tested. These amounts correspond themselves to a dosage of application to the skin or scalp of 1%, 2% and 3% of the above active ingredient of point B).

1. Reducing the Proliferation of Germs Involved in the Formation of Dandruff a) Action on the Production of an Antimicrobial Natural Peptide (hBD2)

To control the perturbation of its microbial flora, scalp produces antimicrobial natural peptides (PAM) to reduce the proliferation of germs (bacteria, yeast) and their harmfulness. PAM therefore protects the scalp. One of them, the beta-defensin 2 peptide (hBD2) is produced by skin cells and acts by perforating the cell walls of bacteria or yeast.

Principle:

Human keratinocytes were grown to mid-confluence for 4 days and receive the product according to the invention in their culture medium, the medium being changed regularly. At the end of the contact, the cells were lysed and the levels of hBD2 are assessed by ELISA. The number of cells is estimated in parallel with a DNA dye for quantifying cells and normalize the data.

TABLE 1

Modulation of the production of the antimicrobial peptide hBD2 in the keratinocytes in contact with the extract according to the invention for 4 days (n = 3).

|  |  | hBD2; pg/mL/10$^6$ cell. | Variation (%) |
| --- | --- | --- | --- |
| Control |  | 205 +/− 55 | Reference |
| Extract | 8 ppm | 317 +/− 36 | +55%; p < 0.05 |
| according to the | 16 ppm | 385 +/− 35 | +88%; p < 0.01 |
| invention | 24 ppm | 447 +/− 36 | +118%; p < 0.01 |

No cytotoxic effect noted.

The results show that the extract, according to the invention can increase significantly and dose-dependently the production of the antimicrobial peptide hBD2 and thus can inhibit the proliferation of microorganisms involved in dandruff.

b) Action on the Production of a Microbial Receptor (TLR9)

Epithelial cells have at their external surface or on the surface of their endosomes receptor called Toll-Like (or TLR). These structures play a crucial role in innate immunity of the skin. They aim indeed to capture the bacteria, yeast and viruses and trigger an immune response. But too abundant, they promote inflammation. Besides TLR2 and 4, well known and extracellular, TLR-9 is found especially in keratinocytes and is involved in the recognition of several yeast including *Malassezia furfur* and *Malassezia globasa*, responsible for the formation of dandruff.

Principle:

Skin explants (5 mm diameter) from 4 female donors (mean 69 years (45-90 years)) are brought into contact for 3 days, in their culture medium, with a *Malassezia* yeast suspension. After removal of the yeast suspension, the skins received every day, for 3 days, an after-shampoo solution not rinsed ("Leave-on"; formula 1.2 of below § D Galenics) containing an extract of *Apium graveolens* according to the invention (corresponding to a dose of 15 ppm of total phthalides), or the placebo. After rinsing, the skins are cut and a TLR-9 marking is performed on these sections.

TABLE 2

Modulation of the expression of TLR9 in skin explants after contact with *Malassezia*, effect of the extract according to the invention and its placebo (n = 4; 12 photos/donor).

| | TLR-9; AFU* | Variation (%) | Variation (%) |
|---|---|---|---|
| Control | 23.0 +/− 5.5 | Reference 1 | — |
| *Malassezia* then « Leave-on» placebo | 25.9 +/− 6.7 | +12.6%, p < 0.05 | Reference 2 |
| *Malassezia* then « Leave-on» according to the invention | 21.8 +/− 4.3 | — | −16%; p < 0.01 |

*AFU: Arbitrary Fluorescence Unit.

Contact with *Malassezia* yeast increased TLR-9 labeling in the explants. Use of the extract according to the invention enabled to control the increase (−16%) significantly compared to placebo (p<0.01). Both tests show that the extract according to the invention disadvantages the metabolism of yeast responsible for dandruff formation and thus allows purifying and embellishing the scalp.

2. Reducing the Sebum Production

Oily skin is associated with a too abundant sebum production by the cells called sebocytes. Too much sebum often leads to modify the properties of the skin and scalp.

Sebum "glues" dead skin, traps bacteria and yeast (like *Malassezia furfur* at the scalp level, causing dandruff) that feed on and proliferate.

Decrease of Lipid Synthesis in the Sebocyte

Principle:

Human sebocytes (26 years female, face) were seeded in their growth medium. At confluence, the cells were putted in contact with the extract according to the invention for 48 hours. After removing media, monolayers were incubated with Nile Red marker of intracellular lipids which estimates the amount of lipids in the cells. The estimate of the viability is performed in parallel on the same layers using a fluorescent dye.

TABLE 3

Modulation of lipid synthesis in sebocytes in the presence or not of the extract according to the invention (n = 3).

| | | Lipids; AFU*/$10^6$ cell. | Variation (%) |
|---|---|---|---|
| Control | | 282975 +/− 11632 | Reference |
| Extract according to the invention | 8 ppm | 255691 +/− 7322 | −10%; p < 0.05 |
| | 16 ppm | 198976 +/− 9368 | −30%; p < 0.01 |
| | 24 ppm | 169424 +/− 433 | −40%; p < 0.01 |

*AFU: Arbitrary Fluorescence Unit; no cytotoxic effect noted.
Linoleic acid: +66% of lipids These results show that exposure of sebocytes to the extract according to the invention can significantly reduce and dose-dependently the amount of lipids in the cells that produce the sebum.

The extract according to the invention can be used to treat skin disorders associated with oily skin or with an oily tendancy, like shiny or glossy aspect, size and number of pores.

The scalp can be "cleaned up" with less sebum, ground for bacteria and yeasts, and traps for dandruff.

3. Reinforcement of the Skin Barrier and its Functions

The scalp of people with a dandruff state presents cells that are poorly differentiated, little cornified and less cohesive, presents less prevalence of ceramide type lipids, an increased transepidermal water loss and a disruption of hydration. Improvement of the skin barrier upstream also helps prevent a dandruff state.

a) Preliminary Study on DNA-Array

A DNA-Array study on normal human keratinocytes in contact with the extract of the invention showed the induction of several genes associated with the reinforcing of the skin barrier compared to the control.

1) The expression of genes coding for loricrin, involucrin and two forms of filaggrin (filaggrin and filaggrin-2) is increased in contact with the extract according to the invention. These proteins are well known to be major players in the cornification and hydration of the stratum corneum.

2) In parallel, the increase of the expression of the cornuline gene is also observed in contact with the extract according to the invention. This protein, found on the scalp, is a marker of the terminal differentiation of the epidermis. Its importance in the homeostasis of the stratum is underlined by the fact that it is reduced in eczema, a chronic inflammatory disease skin.

3) Finally, the extract according to the invention increases the production of SPINK5 and, in parallel, moderates the gene expression of KLK6 and 13. Desquamation results from a balance between KLK (Kallikrein-related peptidase), which break the ties of the corneocyte between them and SPINK5 (Serine Protease Inhibitor Kazal-type 5) that moderates their activity. Loss of function of SPINK5 causes hyper-desquamation of immature cells and a loss of homeostasis of the stratum corneum.

b) Improvement of the Quality of Keratinocyte Differentiation

Normal human keratinocytes almost at confluence are contacted with the extract according to the invention (8 ppm) in an appropriate culture medium in order to study their differentiation in microscope by following the aspect of the layers. At 3 days, the aspect of differentiation is assessed visually. With the extract according to the invention a marked acceleration of the differentiation is observed with stimulation of the formation of typical structures of the top layers of the epidermis (presence of branched structures characteristic of the protein-lipid rigid matrix and in multilayers of the horny envelope; refractive network).

c) Protein Markers of Epidermal Differentiation

Involucrin, loricrin, filaggrin, LCE3B ("Late Cornified Envelope protein 3B") and SPRR ("small proline-rich region proteins") are among the proteins responsible for the quality of the barrier function confered to the stratum corneum.

Principle:

the same cell layers as those discussed above in the fresh state in part b) are fixed and immunolabeled to visualize the synthesis of these 5 protein markers of epidermal differentiation. 5 photos are made on each of the 3 replicas. A quantification of the labeling is performed by image analysis. A counter-staining of cell nuclei can estimate the number of cells and thus normalize the data.

Involucrin

TABLE 4

Modulating the expression of involucrin by keratinocytes in contact with the extract according to the invention (15 photos/case)

|  |  | Involucrin (AFU*/$10^6$ cell.) | Variation |
|---|---|---|---|
| Control |  | 7.5 +/− 9.4 | Référence |
| Extract accrording to the invention | 8 ppm | 206 +/− 94 | x27; p < 0.01 |
|  | 16 ppm | 1134 +/− 291 | x151; p < 0.01 |
|  | 24 ppm | 1014 +/− 74 | x135; p < 0.01 |

*AFU: Arbitrary Fluorescence Unit; no cytotoxic effect noted.

Loricrin

TABLE 5

Modulating the expression of loricrin by keratinocytes in contact with the extract according to the invention (15 photos/case)

|  |  | Loricrin (AFU*/$10^6$ cell.) | Variation |
|---|---|---|---|
| Control |  | 39 +/− 28 | Reference |
| Extract according to the invention | 8 ppm | 149 +/− 76 | x3.8; p < 0.01 |
|  | 16 ppm | 491 +/− 369 | x12.6; p < 0.01 |
|  | 24 ppm | 1161 +/− 501 | x29.8; p < 0.01 |

*AFU: Arbitrary Fluorescence Unit; no cytotoxic effect noted.

Filaggrin

TABLE 6

Modulating the expression of filaggrin by keratinocytes in contact with the extract according to the invention (15 photos/case)

|  |  | Filaggrin (AFU*/$10^6$ cell.) | Variation |
|---|---|---|---|
| Control |  | 182 +/− 150 | Reference |
| Extract according to the invention | 8 ppm | 460 +/− 263 | +153%; p < 0.01 |
|  | 16 ppm | 613 +/− 182 | +237%; p < 0.01 |
|  | 24 ppm | 347 +/− 138 | +91%; p < 0.01 |

*AFU: Arbitrary Fluorescence Unit; no cytotoxic effect noted.

In parallel, the production of the protein SPRR2B (SPRR marker) is increased in the keratinocytes in culture of 103% to 139% (p<0.01) in contact of 16 to 20 ppm of the extract according to the invention compared to the control.

In addition, the LCE3B, induced when it is necessary to repair the skin barrier, show an increased production of +41% to +70% (p<0.01) with 16 to 24 ppm of the extract according to the invention.

All these results are consistent to show the interest of the *Apium graveolens* seed extract according to the invention in the establishment, reinforcement and restoration of the skin barrier. Protein markers known for the quality of the formation of this barrier: involucrine, loricrin, filaggrins, but also SPRR2B or LCE3B, are all increasing thanks to the extract according to the invention.

d) Epidermal Lipids: Cholesterol, Ceramide 2 and Neutral Free Fatty Acids

The scalp of persons with dandruff is characterized by lower levels of intercellular lipids in the horny layer (including ceramides, cholesterol and neutral lipids). This contributes to the weakening of the skin barrier.

Cholesterol

The DNA-Array study also showed, in the presence of the extract according to the invention, the induction of the CYP51A1 gene, encoding a protein of the cytochrome P450 family, which participates in cholesterol synthesis by catalyzing the removal of the lanosterol 14alpha-methyl group.

Neutral Lipids

A similar culture to that carried out for proteins (above) is labeled with a specific dye of neutral lipids (cholesterol and derivatives, triglycerides and fatty acid). After photos, an image analysis can estimate the amount of neutral lipids. The amount of cells was estimated using a counterstain of the nuclei.

TABLE 7

Modulation of the production of neutral lipids by keratinocytes in contact with the extract according to the invention (15 photos/case)

|  |  | Lipids (AFU*/$10^6$ cell.) | Variation |
|---|---|---|---|
| Control |  | 22 +/− 11 | Reference |
| Extract according to the invention | 8 ppm | 132 +/− 85 | x6; p < 0.01 |
|  | 16 ppm | 233 +/− 68 | x10.6; p < 0.01 |
|  | 24 ppm | 230 +/− 71 | x10.5; p < 0.01 |

*AFU: Arbitrary Fluorescence Unit; no cytotoxic effect noted.

Ceramides on Keratinocyte Culture and Explants

A similar culture to that performed above is labeled with an antibody specific of ceramide 2. After taking the photos, image analysis can estimate its amount. The amount of cells was estimated using a counterstain of the nuclei.

Moreover, the same 4 explants as those used for the TLR9 study are immuno-marked to reveal changes in ceramide 2 content. After photos (n=12), an image analysis can quantify them.

TABLE 8

Modulation of the production of ceramics 2 by keratinocytes and explants in contact with the extract according to the invention (15 photos/case)

|  | Keratinocytes | | Explants | |
|---|---|---|---|---|
|  | Ceramide 2* | Variation | Ceramide 2* | Variation |
| Control/placebo | 456 +/− 471 | Reference | 18.9 +/− 7.2 | Reference |
| Extract according to the invention** | 944 +/− 364 | +107%; p < 0.01 | 26.4 +/− 11.2 | +40%; p < 0.01 |

*in AFU $10^6$ cell.: Arbitrary Fluorescence Unit; no cytotoxic effect noted.
**Extract according to the invention: 16 ppm for the keratinocytes; 24 ppm in the «Leave-on» solution for the explants.

In addition to the increase of expression of an enzyme involved in the formation of cholesterol, the increase in neutral lipids and ceramide 2, components of the skin barrier, is noted. These results thus show that contact with the extract according to the invention strengthens the lipid composant of the skin barrier.

4. Soothing the Scalp—Reduction of Irritants Signals a) Effect of the Extract of the Invention on the Production of IL-8

IL-8 is a mediator produced inter alia by keratinocytes in response to the detection of microbial or chemical agents or following UV treatment. The IL-8 guides the immune cells to the origin of the irritation and high levels of IL-8 are found in the squams of people with dandruff. With histamine, it is one of clear markers of dandruff.

Yeast, because of their lipase, excretes irritating lipid byproducts of unsaturated fatty acids type or substrates for the eicosanoid pathway. A model solution of these lipid byproducts (SPL) is prepared and used to assess the soothing properties of the extract according to the invention.

Principle:

Normal human keratinocytes brought almost to confluence are contacted 24 h with the growth medium containing or not containing the extract according to the invention. The media are replaced by the same media supplemented or not with the SPL model solution. After 24 hours, the supernatants were assayed for their content of IL-8 and an estimate of the number of cells is made by the MTT method.

TABLE 9

Modulation of the production of IL-8 by keratinocytes after contact with SPL - Effect of the extract according to the invention (n = 5).

| | | Without SPL | | With SPL | |
|---|---|---|---|---|---|
| | | IL-8 (pg/$10^6$ cell.) | Variation (%) | IL-8 (pg/$10^6$ cell.) | Variation (%) |
| Control | | 1012 +/− 172 | Reference 1 | 1639 +/− 518 | +62%; Reference 2 |
| Extract according to the invention | 16 ppm | 597 +/− 374 | −41%, $p < 0.01$ | 982 +/− 130 | −40%; $p < 0.01$ |
| | 20 ppm | 408 +/− 88 | −60%, $p < 0.01$ | 796 +/− 103 | −51%; $p < 0.01$ |
| | 24 ppm | 249 +/− 32 | −75%, $p < 0.01$ | 569 +/− 100 | −65%; $p < 0.01$ |

* no cytotoxicity was observed

The SPL increase the production of IL-8 by keratinocytes (+62%; $p<0.01$), thus modeling what is observed in dandruff states. The extract according to the invention can clearly and significantly reduce the overproduction of 40 to 65% ($p<0.01$). Moreover, the extract of the invention also reduced markedly and significantly the basal production of IL-8 41 to 75% ($p<0.01$).

5. Action on Dermal Extracellular Matrix—Stimulation of Collagen Synthesis

The extracellular matrix is the center piece of maintaining the skin vitality and viscoelastic properties of the dermis. The components of this matrix undergo qualitative and quantitative structural changes over time and under the effect of free radical processes (mainly the sun, pollution and poor living conditions), leading to skin aging and the appearance of fine lines and wrinkles.

Collagen I is a crucial element for the balance of this matrix. Its production decreases with age, and its fibers are degraded by endogenous and exogenous radical processes. UVs also stimulate the synthesis of certain proteolytic enzymes that degrade the proteins of the extracellular matrix. This results in a loss of firmness, elasticity and skin density. So collagen stimulation is a key factor in the cosmetic treatment for beautifying the skin.

Principle:

Normal human fibroblasts (NHF) are cultured for 24 h. The cells are contacted or not with the products to be tested or their excipient at various concentrations for 7 days. The synthesis of type I collagen produced by the cells in the form of extracellular matrix is then quantified by immuno-marking on the fixed layers. A count of nuclei labeled with Hoechst is performed in parallel in order to have an estimate of the viability and to weight the data.

TABLE 10

Stimulating the synthesis of collagen I by fibroblasts, after contact with the extract according to the invention

| Product | Concentration | % de variation/ control | Significance (Student test) |
|---|---|---|---|
| Extract according to the invention | 10 ppm | +388% | $p < 0.01$ |
| | 15 ppm | +404% | $p < 0.01$ |
| | 20 ppm | +472% | $p < 0.01$ |

D) Galenic

Various cosmetic formulations are described below. Additional active ingredients, coming when appropriate in support and/or in addition to the activity of the active ingredient according to the invention can be added in the correct formulation part according to their hydrophobic or hydrophilic nature. These ingredients can be of any category according to their(s) function(s), site of application (body, face, neck, chest, hands, etc.), the desired end and the targeted consumer.

Active ingredient according to the invention used in the galenic formulations given below: $CO_2$ supercritic extract of *Apium graveolens* seeds included in an ester oil of Caprylic/Capric Triglyceride type so as to be at the end at 500 ppm of total alkyl phthalides.

This ingredient is preconized between 0.1 and 10%, preferably between 1 and 5%, more preferably between 2 and 3%.

1) Scalp Treatment 1.1 Shampoo

| PRODUCT | % | INCI NAME |
|---|---|---|
| Part A | | |
| $H_2O$ | qsp100 | Water |
| Citric acid | 0.15 | Citric Acid |
| Trisodic citrate | 1.20 | Sodium Citrate |
| Part B | | |
| Cremophor RH60 ™ | 3.00 | PEG-60 Hydronegated Castor Oil |

-continued

| PRODUCT | % | INCI NAME |
|---|---|---|
| Ingredient according to the invention | 2.00 | |
| Part C | | |
| Texapon NSO UP ™ | 20.00 | Sodium Laureth Sulfate |
| Crodateric CAB-30 LQ-(MH) ™ | 5.00 | Cocamidopropyl Betaine |
| Phenoxyethanol | qs | Phenoxyethanol |
| Perfume | 0.10 | Fragrance |
| Crothix Liquid LQ-(RB) ™ | 3.00 | PEG-150 Pentaerythrityl Tetrastearate & PEG-6 Caprylic/Capric Glycerides & Aqua |

Protocol:
Weigh part A and heat at 75° C. in a water bath. Mix well. Weigh part B and heat at 75° C. in a water bath. Mix well. Add part B to part A under stirring. Add the ingredients of part C, one by one, in the previous part under stirring. Mix well.

Examples of active ingredient, marketed by Sederma, that can be added to this formulation:

CERAMIDE A2 PH™: chemical analogue of ceramide 2, a naturally occurring molecule of the hair. Acting by strengthening the hair structure, protecting and sheathing damaged hair, including colored or permed hair.

CAPIGENE SP™: ingredient comprising three complementary actives: homotaurine, a bacterial filtrate rich in peptides and sulfomucopolysaccharides extract of marine origin. Acts by slowing hair loss, stimulating the renewal and regeneration of hair and involved in the regulation of seborrhea often implicated in alopecia phenomena. Contributes to the health and strength of the scalp and hair.

HELIOGENOL™: hydro glycolic extract of sunflower seeds titrated in polyphenols. Naturaly comprises a free radical captor. Protects and repairs the natural and colored hair against the aggression of shampoos and UV rays.

CAPILECTINE SP™: glycoprotein with a molecular weight of about 20,000 daltons, purified from *Solanum tuberosum* L. which has similar characteristics to those of lectins. Stimulates hair vitality.

1.2 «Leave on»

| PRODUCT | % | INCI NAME |
|---|---|---|
| Part A | | |
| H$_2$O | Qsp100 | Water |
| Citric acid | 0.15 | Citric Acid |
| Trisodic citrate | 1.20 | Sodium Citrate |
| Potassium sorbate | Qs | Potassium Sorbate |
| Keltrol CG-SFT ™ | 0.30 | Xanthan Gum |
| Part B | | |
| Cremophor RH60 ™ | 0.40 | PEG-60 Hydronegated Castor Oil |
| Ingredient according to the invention | 3.00 | |
| Part C | | |
| Ethanol 96° | 5.00 | Glycerin |
| Phenoxyethanol | qs | Phenoxyethanol |
| Perfume | 0.10 | Fragrance |
| Part D | | |
| Incroquat CTC-30 LQ-(MH) ™ | 1.00 | Cetrimonium Chloride |

Protocol:
Sprinkle xanthan gum under rapid stirring into part A and let rise for 30 minutes. Heat part A at 75° C. in a water bath. Weigh part B and heat at 75° C. in a water bath. Mix well. Add part C, below 35° C., mix well. Add part C in the previous part under stirring; mix well. Add part D slowly. Mix well.

Examples of active ingredient, marketed by Sederma, that can be added to this formulation: as previously for the shampoo, and/or PACIFEEL™: active ingredient actif marketed by Sederma, comprising a natural extract of the *Mirabilis jalapa* plant also known as the Marvel of Peru, which alleviates cutaneous discomfort, fades redness of sensitive and reactive skin and strengthens and hydrates the epidermis.

1.3 Tonic Emulsion

| PRODUCT | % | INCI NAME |
|---|---|---|
| Part A | | |
| H$_2$O | Qsp100 | Water |
| Citric acid | 0.15 | Citric Acid |
| Trisodic citrate | 1.20 | Sodium Citrate |
| Potassium sorbate | qs | Potassium Sorbate |
| Part B | | |
| Butylen glycol | 2.00 | Butylen Glycol |
| Keltrol CG-SFT ™ | 0.30 | Xanthan Gum |
| Part C | | |
| Cremophor RH60 ™ | 3.50 | PEG-60 Hydronegated Castor Oil |
| Ingredient according to the invention | 3.00 | |
| Part D | | |
| Phenoxyethanol | qs | Phenoxyethanol |
| Perfume | 0.10 | Fragrance |
| Part E | | |
| Incroquat CTC-30 LQ-(MH) ™ | 2.00 | Cetrimonium Chloride |

Protocol:
Weigh part A. Mix under stirring. Weigh part B and homogenize. Add part B to part A under stirring. Let rise for 30 minutes. Heat part A+B at 55° C. in a water bath. Weigh part C and heat at 55° C. in a water bath. Add part C into part A+B under rapid stirring. Add part E in the previous part under gentle agitation. Mix well.

An opaque fluid emulsion is obtained.

Examples of active ingredient, marketed by Sederma, that can be added to this formulation:

PROCAPIL™: anti-hair-loss active ingredient marketed by Sederma (WO00/58347) that combines a vitamin matrikine (biotinyl-GHK), apigenin (a flavonoid extracted from *citrus*) and oleanolic acid (root extract from *Loveyly Hemsleya*).

1.4 Smoothing Serum (Cream Emulsion)

| PRODUCT | % | INCI NAME |
|---|---|---|
| Part A | | |
| H$_2$O | Qsp100 | Water |
| Optasense G83 ™ | 0.20 | Carbomer |
| Part B | | |
| Zémea ™ | 5.00 | Propanediol |
| Phenoxyethanol | qs | Phenoxyethanol |

-continued

| PRODUCT | % | INCI NAME |
|---|---|---|
| Part C | | |
| Ingredient according to the invention | 3.00 | |
| Pemulen TR-2 ™ | 0.20 | Acrylates/C10-30 Alkyl Acrylate Crosspolymer |
| Part D | | |
| Potassium sorbate | qs | Potassium Sorbate |
| Part E | | |
| H₂O | 3.00 | Water |
| NaOH 30% | 0.30 | Sodium Hydroxyde |
| Part F | | |
| Ethanol 96 surfin | 8.00 | |
| Perfume | 0.10 | |

Protocol: Part A: sprinkle carbomer in water. Let swell 30 minutes. Weigh part B and mix. Add part B and mix. Add part B to part A under normal agitation. Weigh part C and mix. Add part C to part A+B. Homogenize under stronger stirring. Weigh part D. Extemporaneously pour part D into part A+B+C under stirring. Neutralize with part E to pH=5.60+/−0.10 under normal agitation. Weigh part F and stir. Add part F in the previous part under normal agitation.

1.5 Mask

| PRODUCT | % | INCI NAME |
|---|---|---|
| Part A | | |
| H₂O | Qsp100 | Water |
| Potassium sorbate | qs | Potassium Sorbate |
| Part B | | |
| Rejuvasoft-PA-MH ™ | 6.00 | Polyquaternium-91 & Cetearyl Alcohol & behentrimonium Chloride & Myristyl Myristate |
| Terraquat BD-PA-MH ™ | 1.00 | Bis-(Ethyl PPG-3 Behenate) Dimonium Methosulfate & Behenamidopropyl Dimethylamine |
| Crodacol CS90-PA-(RB) ™ | 2.00 | Cetearyl Alcohol |
| Ingredient according to the invention | 3.00 | |
| Part C | | |
| Glycerin | 3.00 | Glycerin |
| Phenoxyethanol | qs | Phenoxyethanol |
| Part D | | |
| Perfume | 0.10 | Fragrance |

Protocol:

Weigh part A. Heat at 85° C. in a water bath. Weigh part B and heat at 85° C. in a water bath. Weigh part C and homogenize. Add part C to part A under stirring. Add part B to part A+C under rapid stirring for 30 s. Add part D at 35° C. under stirring.

An opaque viscous cream is obtained.

Examples of active ingredient, marketed by Sederma, that can be added to this formulation:

HAIRSPA™: Scalp moisturisation and soothing active ingredient comprising lactitol and xylitol in glycerin, acts on skin microflore balance to fight against scalp discomfort (dryness, itching, dandruff, irritations).

FRUITBIO™: Complex of α-hydroxy acids associated with green tea extract. Smoothing hair cuticle.

1.6 Oil

| PRODUCT | % | INCI NAME |
|---|---|---|
| Part A | | |
| BRB CM 56 ™ | Qsp100 | Cyclopentasiloxane & Cyclohexasiloxane |
| XIAMETER PMX 200 5cs ™ | 6.00 | Dimethicone |
| BRB PTM 20 ™ | 2.00 | Phenyltrimethicone |
| Crodamol DA-LQ-(RB) ™ | 10.00 | Diisopropyl Adipate |
| Arlamol HD-LQ-(RB) ™ | 5.00 | Isohexadecane |
| Crodamol TN-[EU]-LQ-(JP) ™ | 5.00 | Isotridecyl isononanoate |
| Ingredient according to the invention | 3.00 | |
| Part B | | |
| Phenoxyethanol | qs | Phenoxyethanol |
| Perfume | 0.20 | Fragrance |
| Ethanol 96° | 5.00 | Alcohol |

Protocol: Weigh part A and put under gentle stirring. Weigh part B and homogenize. Add part B into part A under gentle stirring. Mix well.

A colorless clear oil is obtained.

1.7 Cleansing Conditioner

| PRODUCT | % | INCI NAME |
|---|---|---|
| Part A | | |
| H₂O | Qsp100 | Water |
| Potassium sorbate | Qs | Potassium Sorbate |
| Incromide Oxide C-LQ-(MH) ™ | 2.00 | Cocamidopropylamine Oxide & Water |
| Lustreplex-LQ-(MH) ™ | 1.50 | Polyquaternium-70 & Dipropylene Glycol |
| Part B | | |
| Crodazoquat MCC-PA-MH ™ | 1.50 | Behentrimonium Methosulfate & Cetearyl Alcohol & Quaternium-86 |
| Crodacol CS-PA-(RB) ™ | 3.00 | Cetearyl Alcohol |
| Ingredient according to the invention | 2.00 | |
| Part C | | |
| Glycerin | 3.00 | Glycerin |
| Crovol A70-LQ-(RB) ™ | 1.00 | PEG-60 Almond Glycerides |
| Phenoxyethanol | qs | Phenoxyethanol |
| Part D | | |
| Perfume | 0.10 | Fragrance |

Protocol: Weigh part A and heat in a water bath at 85° C. Weigh part B and heat in a water bath at 85° C. Weigh part C and homogenize. Add part C to part A under normal agitation. Add part B to part A+C under rapid stirring. Add part D at 35° C. under stirring and mix well.

Example of active ingredient, marketed by Sederma, that can be added to this formulation:

CERAMIDE A2 PH™

1.8 Biphasic Spray

| PRODUCT | % | INCI NAME |
|---|---|---|
| Part A | | |
| H₂O | Qsp100 | Water |
| Potassium sorbate | qs | Potassium Sorbate |

-continued

| PRODUCT | % | INCI NAME |
|---|---|---|
| Part B | | |
| Crovol A70-LQ-(RB) ™ | 1.00 | PEG-60 Almond Glycerides |
| Phenoxyethanol | qs | Phenoxyethanol |
| Part C | | |
| Crodamol DA-LQ-(RB) ™ | 24.00 | Diisopropyl Adipate |
| Crodamol TN-[EU]-LQ-(JP) ™ | 3.00 | Isotridecyl Isononanoate |
| Ingredient according to the invention | 3.00 | |
| Perfume | 0.20 | Fragrance |

Protocol: Weigh part A and mix under slow stirring. Weigh part B and homogenize. Add part B to part A. Mix well under rapid stirring. Weigh part C and homogenize. Add part C into part A+B under stirring.

Example of active ingredient, marketed by Sederma, that can be added to this formulation:
FRUIT BIO™
2) Skin Treatment
Face Cream for Oily Skin and/or Antiaging

| PRODUCT | % | INCI NAME |
|---|---|---|
| Part A | | |
| H₂O | Qsp100 | Water |
| Carbopol Ultrez 10 | 0.25 | Carbomer |
| Part B | | |
| Glycerin | 3.50 | Glycerin |
| Part C | | |
| Brij S2 SS | 0.40 | Steareth-2 |
| Brij S10 SO | 1.20 | Steareth-10 |
| Crodafos CES | 4.00 | Cetearyl Alcohol & Dicetyl Phosphate & Ceteth-10 Phosphate |
| Vaseline oil | 2.50 | Mineral Oil |
| Xiameter PMX-0345 | 2.00 | Cyclopentasiloxane & Cyclohexasiloxane |
| Crodamol OSU | 7.00 | Diethylhexyl Succinate |
| Preservative | qs | — |
| Part D | | |
| Ingredient according to the invention | 3.00 | |
| Part E | | |
| Potassium sorbate | 0.10 | Potassium Sorbate |
| Part F | | |
| H₂O | 4.00 | Water |
| NaOH 30% | 0.40 | Sodium Hydroxide |
| Part G | | |
| Perfume | 0.10 | Fragrance |

Protocol:
Part A: Sprinkle Carbomer in water and let swell for 1 hour without stirring. Weigh and add part B into part A. Homogenize. Heat part A+B in a water bath at 75° C. Weigh and heat part C in a water bath at 75° C. Mix well. Weigh part D. Add part D into part C, homogenize. Add part C+D in part A+B under stirring. Extemporaneously, add part E in the emulsion under stirring. Add part F in the emulsion. Cool under stirring. Adjust pH to 5.90+/−0.10 using part F, below 35° C. Add part G, mix well.

Examples of active ingredient, marketed by Sederma, that can be added to this formulation:
MATRIXYL™3000: peptide-based anti-wrinkle ingredient marketed by Sederma (WO2005/048968) comprising two matrikines Pal-GHK and Pal-GQPR, which in synergy helps repairing skin damages caused by aging.
MATRIXYL synthe'6™: peptide-based anti-wrinkle ingredient marketed by SEDERMA which helps repair skin damage caused by aging.
PACIFEEL™
Ac-Net™: an active sold by SEDERMA (WO2003/02828692) offering a complete treatment of oily and acne-prone skins.
EVERMAT™: active marketed by SEDERMA (WO2007/029187), which decreases the secretion of sebum and thus participates in the treatment of oily skin.

E) In Vivo Tests
Principle
Two separate studies were conducted on a total of 106 volunteers:
Study A on a panel of 46 volunteers, mean age 38 years [21-59 years], with sensitive scalp, itching and dandruff in most cases.
Study B on a panel of 60 volunteers, mean age 38 years [19-63 years], half with oily dandruff and half with dry dandruff, and itching in almost all cases.

The evaluation of the efficacy of the extract according to the invention was conducted on their scalp around three major axes:
1. Improvement of dandruff states:
By a dermatologist assessment,
Visualization on macrophotos,
A quantization by confocal laser microscopy and
A self-assessment
2. The restoration of skin barrier:
With a measure of the TEWL using a VapoMeter,
Of Hydration using a DermaLab™ and Corneometer™ and
Of sebum rate using a Sebumeter
3. The decrease of itching:
With a dermatologist evaluation and
A self-assessment Protocol
Particular Inclusion Criteria
For the 2 studies, volunteers have observed a period of "wash-out" with a neutral shampoo. Hormonal constancy during the 3 months before the test and during the test was asked to women. During the test, moderate sun exposure, the exclusive use of hair products supplied and refrain from going to the hairdresser were requested.

Study Type and Duration
Studies were conducted single-blind on the whole scalp. The treatment consisted in use, at least 3 times per week, for 3 weeks, a shampoo and then a non-rinsed after-shampoo lotion (or "Leave-on") either placebo either comprising 2% respectively (shampoo) and 3% ("Leave-on") of the ingredient comprising the extract according to the invention (according to formulas 1.1 and 1.2 given above in § D).

The synopsis of the study can be summarized according to the following diagram.

| T0 | T 7 days (Study B only) | T 21 days |
|---|---|---|
| Dandruff | Dandruff | Dandruff |
| Dermatologist | Dermatologist | Dermatologist |
| Macrophotos | . . . | Macrophotos |
| Confocal microscopy | . . . | Confocal microscopy |
| . . . | Self-assessment | Self-assessment |

| T0 | T 7 days (Study B only) | T 21 days |
|---|---|---|
| Barrier | Barrier | Barrier |
| VapoMeter ™ DermaLab ™ Corneometer ™ Sebumeter ™ | . . . . . . Corneometer ™ Sebumeter ™ | VapoMeter ™ DermaLab ™ Corneometer ™ Sebumeter ™ |
| Itching | Itching | Itching |
| Dermatologist . . . | Dermatologist Self-assessment | Dermatologist Self-assessment |

Statistical studies were performed using the Student's t test or, if needed, a Wilcoxon or Mann-Whitney non-parametric test. To compare the effect to T0, two-sided tests were performed on paired series. To compare two products, two-sided tests were performed on non-paired series. A Chi2 test was used for the questionnaire evaluation.

Results

1) Evaluation of Dandruff a) Clinical Evaluation by a Dermatologist (Study B)

At each interval, a dermatologist assessed the number and size of the dandruff according to the following table:

| | |
|---|---|
| 7 | Numerous and large |
| 6 | Numerous and small |
| 5 | Large |
| 4 | Small |
| 3 | Few and large |
| 2 | Few and smal |
| 1 | None |

These results show that using the treatment with the products of the invention leads to a clear reduction in dry and oily dandruff compared to T0 and compared to the placebo. After 3 weeks, the scores are improved by 61% (dry dandruff, p<0.01 vs. placebo) and 64% (oily dandruff, p<0.05 vs. placebo). Scalp condition became almost normal with few small scales (scores of 2.0 and 1.9).

Using the placebo treatment did not lead to a significant reduction in dry dandruff (score decreasing from 5.0 to 4.2) and, in the oily dandruff, to a lesser score reduction score (from 5.1 to 3.9 p<0.01) than obtained with the products of the invention.

Advantageously, efficacy was noted after just 7 days on both types of dandruff, with −31% for oily dandruff (p<0.01 vs. T0) and −20% for dry dandruff (p<0.05 vs. T0).

b) Self-Evaluation by Volunteers (Study B)

At the same time, the volunteers assessed the effects of the treatment themselves. The results support the dermatologist's analysis.

After 3 weeks of application:

Whether for the dry or oily dandruff, 93% of the volunteers applying the treatment with the products of the invention saw a significant improvement in their condition (less dandruff) compared to T0 (p<0.01). These values are also significant compared to the placebo (p<0.01 andp<0.05).

They are far fewer to see an improvement with the placebo (40% for dry and 53% for oily skin; not significant in 2 cases).

A much higher proportion (73 to 80%) even saw their dandruff disappear following the treatment with the products of the invention. The difference with the panel having applied a placebo is very clear, significant (p<0.05).

c) Evaluation on Macrophotos (Study A)

Dandruff was visualized and evaluated by eight experts on standard photos taken using a dermoscopic camera, Viva-Cam® (Mavig GmbH VivaScope Systems, Germany). Each image contains 1600×1200 pixels for a 9×7 mm measurement field.

The photos of the volunteers showing clearly visible and sufficient dandruff at T0 were selected for the analysis, therefore a total of 17 volunteers for the product and 17 volunteers for the placebo (around 70% of the panel). The photos taken after 3 weeks were compared to those from T0 and the experts were to respond to the following assertion: "the scalp shows less scale after treatment".

In the panel having used the products according to the invention, 68% of responses point towards a reduction in scales was noted. The 68% response rate is significantly different from all non-positive responses (8% Do not agree +24% Neither agree nor disagree). Furthermore, a significant difference compared to the placebo panel was noted on which only 35% of responses are in favor of an improvement in dandruff, the undecided being almost twice as many than for the panel having applied the products of the invention (46% vs. 24%).

d) Evaluation by Confocal Microscopy (Study A)

It is commonly accepted that subjects with confirmed dandruff have a hyperproliferative epidermis and a thicker albeit imperfect stratum corneum. In order to assess the effect of the products of the invention on this parameter, the thickness of the stratum using a confocal laser microscope (VivaScope® 3000; Mavig GmbH, Germany) was measured.

The laser light emitted by this device in the skin is reflected differently according to the structures with which it comes into contact (keratin, melanin, collagen). A specific optical system is used to reconstitute a clear image of these structures at a chosen depth. Horizontal optical sections of the epidermis and dermis, a few microns apart in depth, are thus obtained.

During this study, images were acquired at different depths at 2.6 µm intervals in order to reproduce the entire epidermis and the stratum corneum in particular.

TABLE 10

Evaluation of the thickness of the *stratum corneum* on the scalp after 3 weeks of application of the products according to the invention (n = 23) or placebos (n = 22)

| | Products of the invention | | Placebos | |
|---|---|---|---|---|
| | T0 | T 3 weeks | T0 | T 3 weeks |
| Mean (µm) +/− Sd | 20.3 +/− 5.8 | 17.6 +/− 4.4 | 19.7 +/− 4.8 | 21.3 +/− 5.0 |
| % variation vs T0 | | −13.3% | | 8.1% |
| Significance vs. T0 | | p < 0.01 | | p < 0.05 |
| Maximum | | −47% | | |
| Responders | | 70% | | |
| Significance vs. placebos | | p < 0.01 | | |

Analysis of the results shows an increase of 8.1% (p<0.05) of the stratum corneum thickness after 3 weeks use of the placebos. In parallel the use of the product of the invention causes a significant 13.3% decrease in stratum corneum thickness. This reduction is also significantly different from that which is observed for the placebo (p<0.01). This data would appear to indicate an improvement in stratum corneum quality thanks to the product of the invention, and the TEWL and hydration results below confirm this.

2) Evaluation of the Cutaneous Barrier

It is known that the quality of the cutaneous barrier of the scalp is related in particular to a good transepidermal water loss value (or TEWL) and a good hydration.

TEWL measurement was conducted in study A. Two hydration measurements were conducted respectively on the panel of study A and on the panel on dry dandruff of study B.

a) TEWL Measurement by the VapoMeter™ (Study A)

Plastic stencils and anatomical landmarks were used to mark out the specific areas on the scalp. TEWL was measured nine times (3 per site×3 sites) using the VapoMeter™ (Delfin Technologies, Finland) on the same sites at T0 and after T3 weeks.

significant at p<0.05 vs. placebos. This data therefore shows the beneficial and restructuring effect of the products according to the invention on the scalp skin barrier.

b) Evaluation of the Scalp Hydration (Study A and B)

Scalp hydration was measured by impedance measurement using a Corneometer® (C&K, Germany) for the dry dandruff panel of study B and using a DermaLab® with pin probe (Cortex, Denmark) for the complete panel of study B. The DermaLab® is especially suitable for measuring scalp hydration due to the structure of its eight-pin probe with 6 mm pins for easy access to the scalp and which prevents water collection on the probe.

Measurements on the Corneometer® were carried out three times on the hair line whereas the DermaLab® measurements were carried out three times on two separate sites on the scalp.

TABLE 12

Evaluation of the hydration of the scalp after 1 and 3 weeks of application of the products according to the invention or placebos.

| | Corneometer | | | | | | Dermalab | | | |
|---|---|---|---|---|---|---|---|---|---|---|
| | Placebos | | | Products according to the invention | | | Placebos | | Products according to the invention | |
| | T0 | T1s. | T3s. | T0 | T1s | T3s. | T0 | T3s. | T0 | T3s. |
| Mean | 34.3 | 33.6 | 34.2 | 32.3 | 34.3 | 35.1 | 59.8 | 54.9 | 56.5 | 63.3 |
| +/−Sd | 1.8 | 1.8 | 2.0 | 2.3 | 2.4 | 2.4 | 23.9 | 24.4 | 26.8 | 19.6 |
| % variation vs. T0 | | −2% | −0.3% | | +6.2% | +8.7% | | −8.2% | | +12% |
| Significance vs. T0 | | nds | nds | | p < 0.01 | p < 0.01 | | nds | | p < 0.05 |
| Maximum | | | | | 18% | 19% | | | | 148% |
| Responders | | | | | 100% | 100% | | | | 73% |
| Significance vs. placebos | | — | | | p < 0.01 | p < 0.01 | | — | | p < 0.05 |

Corneometer n = 15 for the 2 cases;
Dermalab: n = 20 for the products according to the invention,
n = 22 for the placebos

TABLE 11

Evaluation of the average TEWL on the scalp after 3 weeks of application of the products according to the invention (n = 20) or placebos (n = 22)

| | Products of the invention | | Placebos | |
|---|---|---|---|---|
| | T0 | T3 weeks | T0 | T3 weeks |
| Mean (g/m²/h) +/− Sd | 18.9 +/− 4.2 | 17.6 +/− 3.8 | 19.9 +/− 4.7 | 20.8 +/− 2.8 |
| % variation vs.T0 | | −6.9% | | +4.5% |
| Significance vs. T0 | | p < 0.07 | | nsd |
| Maximum Responders | | −36% 65% | | |
| Significance vs. placebos | | p < 0.05 | | | nds: non significant difference

These results show that the mean TEWL value is non-significantly increased by +4.5% following use of the placebos. At the same time, on the panel having used the products of the invention for 3 weeks, a 6.9% decrease in mean TEWL is noted, significant at p<0.07 vs. T0 and These results, from two different panels, of which one specifically dry, in two separate studies and using two methods, show that application of the products of the invention increases scalp hydration. On a dry scalp, from 7 days an increase of +6.2% (p<0.01 vs. placebo) and an increase of +8.7% at T3 weeks (p<0.01 vs. placebo) are observed. With the pin probe method, the results show a 12.1% increase (p<0.05 vs. placebo). These results are highly complementary, the difference possibly attributable to the panel, method or the probe.

3) Evaluation of the Sebum Level

As scalp sebum level is a key criterion in the appearance of dandruff. This parameter is also centrally in the profile of an oily skin. It was monitored on the oily dandruff panel of study B using the Sebumeter® (C&K, Germany) which directly measures sebaceous secretion by photometry. The Sebumeter® probe comprises a mirror on which an opaque film is placed and which becomes more or less transparent depending on the sebum adsorbed by it after repeated application to the skin. A photoelectric cell analyses film transparency making it possible to deduce the sebum level. The oily dandruff panel was used for this study.

TABLE 13

Evaluation of sebum content on the scalp after 1 and 3 weeks of application of the products according to the invention (n = 15) or placebos (n = 15).

|  | Products of the invention | | | Placebos | | |
| --- | --- | --- | --- | --- | --- | --- |
|  | T0 | T1 week | T3 weeks | T0 | T1 week | T3 weeks |
| Mean (μg sébum/ cm$^2$) +/− Sd | 182.1+/− 12.5 | 132.5+/− 8.3 | 119.6+/− 8.8 | 166.5+/− 8.6 | 157.8+/− 9.7 | 157.5+/− 10.2 |
| % variation vs. T0 | — | −27.2% | −34.3% | — | −5.2% | −5.4% |
| Significance vs. T0 |  | p < 0.01 | p < 0.01 |  | nds | nds |
| Maximum |  | −47% | −61% |  |  |  |
| Responders |  | 93% | 100% |  |  |  |
| Significance vs. placebos |  | p < 0.01 | p < 0.01 |  |  |  |

The applying of the products of the invention provides a very clear reduction in sebum level of −27%, as from the first week, which is amplified after 3 weeks to reach −34%. These decreases are highly significant compared to T0 ($p<0.01$) and compared to the placebos ($p<0.01$). The condition of the scalp in the subjects with oily dandruff was clearly improved.

4) Itching a) Itching Evaluation by Dermatologist and Self-Evaluation (Study B)

44% of the French population declares to have a sensitive scalp, and besides it is shown that dandruff leads to a prevalence of itching and irritation that is three times higher.

After 1 and 3 weeks use of the products of the invention by the dry and oily dandruff panels, a dermatologist assessed the frequency and intensity of itching on the basis of the volunteers' declarations and according to the following table:

|  | Itching score - Frequency | Itching score - Intensity |
| --- | --- | --- |
| 1 | None | None |
| 2 | Mild (few episodes per day) | Mild |
| 3 | Moderate (some episodes per day) | Moderate |
| 4 | Remarkable (numerous and frequent daily episodes) | Patent |

This study shows that seven days after application of the products of the invention, a reduction in itching, as much on dry or oily scalp, was observed (around −15%, $p<0.05$). This reduction was amplified to reach −40% ($p<0.01$ vs. T0 and $p<0.05$ vs. placebo) after 21 days of treatment. The sensation scores after 21 days of application corresponded practically to no itching. At the same time, application of the placebos provided almost no changes. This analysis applies to both the frequency and the intensity of itching.

At the same time, volunteers also assessed themselves the reduction in irritation and itching and the calming effect of the treatments. The results support the dermatologist's analysis.

In both panels, 100% of volunteers experienced less itching after using the products of the invention, with a much lower percentage after using the placebos (66%). The variation compared to the placebos is significant at $p<0.05$ for both panels. For irritation, the results were also in favor of the products of the invention with 93% (oily dandruff panel) and 100% (dry dandruff panel) decrease compared to just 80% and 60% for the placebos.

Finally, the volunteers mainly agreed on a lasting calming effect after application of the product of the invention (80% and 93%) whereas the placebo only induced this effect on a smaller percentage at 53% in both panels. For the dry dandruff panel, this variation is significant with regard to the placebo panel at $p<0.05$.

b) Histamine on Scalp

In addition to the results on the feelings of the volunteers, histamine in the scales has been evaluated. Histamine is an immune system signaling molecule also found in the skin where it acts on certain receptors and causes pruritus (skin itching). Histamine levels two times higher were observed on the scalp of subjects with dandruff, these quantities clearly reducing following an effective anti-dandruff treatment. The decrease of the level of this substance makes it possible to predict and monitor scalp soothing.

To test the histamine levels, adhesive strips to take samples of scales from subjects with dandruff were used. These samples, which were reproducible, were taken from a line running from the forehead to the vortex, marked according to anatomical landmarks and stencils between T0 and T3 weeks. Once loaded with scales, the adhesive tapes were extracted in a buffer and histamine levels tested using an ELISA kit. At the same time, the BCA method was used to test protein levels in order to normalize the results.

43 samples were taken (3 could not be tested) from 20 people having applied the placebo treatment (shampoo+ leave-on lotion) for 21 days, and from 23 others having used the treatment with the products of the invention (shampoo at 2%+leave-on lotion at 3% of the ingredient comprising the extract according to the invention) with the formulas 1.1 and 1.2 given in the galenic part above.

TABLE 14

Modulating the amount of histamine in dander, effect of the products according to the invention or placebos.

|  | T0; Histamine (nM/mg protein) | T3 weeks; Histamine (nM/mg protein) | Variation vs. T0 (%) | Variation vs. placebos (%) |
| --- | --- | --- | --- | --- |
| Placebos | 7213 +/− 5926 | 6311 +/− 7146 | −13%; nds | — |
| Products of the invention | 7485 +/− 9596 | 4026 +/− 4723 | −46%; p < 0.01 | −33%; p < 0.05 |

The results above show that using the scalp treatment with the products of the invention provides a reduction of the amount of histamine found in the scales. The decrease is important (−46% compared to T0 and significant at $p<0.01$) and significant compared to the placebos (−33%, $p<0.05$). The reduction of this agent, known to cause itching, confirms the self-evaluation and the dermatologist's data.

The invention claimed is:

1. A cosmetic active ingredient comprising in a physiologically acceptable matrix an oily extract comprising a mixture of alkyl-phthalides, as major compounds, prepared by $CO_2$ supercritical extraction of *Apium graveolens* seeds, wherein the mixture of alkyl-phthalides comprises:
   (i) 0-45% by weight of Sedanolide,
   (ii) 45-90% by weight of Sedanenolide, and
   (iii) 0-30% by weight of 3-n-butylphthalide, based on the total weight of the alkyl-phthalides.

2. The ingredient according to claim 1, wherein said extract comprises at least 50% of alkyl-phthalides.

3. The ingredient according to claim 1, wherein said alkyl-phthalide mixture comprises mainly sedanenolide.

4. The ingredient according to claim 3, wherein said alkyl-phthalide mixture comprises at least 50% of sedanenolide.

5. A cosmetic composition comprising at least the cosmetic active ingredient according to claim 1 in a physiologically acceptable excipient.

6. The ingredient according to claim 1, wherein the alkyl-phthalides are in a form bound to or incorporated in or absorbed in or adsorbed on macro-, micro-, and nanoparticles, or macro-, micro-, and nano-capsules, for the treatment of textiles, natural or synthetic fibers, wools, and any materials that may be used for clothing to come into contact with a skin.

7. The ingredient according to claim 1, wherein the physiologically acceptable matrix is a hydrophobic matrix or a combination of a hydrophilic matrix with a surfactant.

8. The ingredient according to claim 1, wherein the physiologically acceptable matrix forms physiologically acceptable medium comprising hydro-alcoholic solution, a water-in-oil emulsion, an oil-in-water emulsion, a micro-emulsion, an aqueous gel, an anhydrous gel, a serum, a dispersion of vesicles, or a powder.

9. The ingredient according to claim 5, wherein the physiologically acceptable excipient comprises an aqueous, a hydro-alcoholic solution, a water-in-oil emulsion, an oil-in-water emulsion, a micro-emulsion, an aqueous gel, an anhydrous gel, a serum, a dispersion of vesicles, or a powder.

10. The cosmetic composition according to claim 5, wherein the cosmetic active ingredient is present in an amount of 0.1-10% by weight in the physiologically acceptable excipient, based on the total weight of the cosmetic composition.

11. The cosmetic composition according to claim 5, wherein the cosmetic composition is a topical composition.

* * * * *

SEQUENCE LISTING

<160> NUMBER OF SEQ ID NOS: 25

<210> SEQ ID NO 1
<211> LENGTH: 4
<212> TYPE: PRT
<213> ORGANISM: artificial sequence
<220> FEATURE:
<223> OTHER INFORMATION: synthetic peptide

<400> SEQUENCE: 1

Arg Ser Arg Lys
1

<210> SEQ ID NO 2
<211> LENGTH: 4
<212> TYPE: PRT
<213> ORGANISM: artificial sequence
<220> FEATURE:
<223> OTHER INFORMATION: synthetic peptide

<400> SEQUENCE: 2

Gly Gln Pro Arg
1

<210> SEQ ID NO 3
<211> LENGTH: 4
<212> TYPE: PRT
<213> ORGANISM: artificial sequence
<220> FEATURE:
<223> OTHER INFORMATION: synthetic peptide

<400> SEQUENCE: 3

Lys Thr Phe Lys
1

<210> SEQ ID NO 4
<211> LENGTH: 4
<212> TYPE: PRT
<213> ORGANISM: Artificial sequence
<220> FEATURE:
<223> OTHER INFORMATION: Synthetic peptide

<400> SEQUENCE: 4

Lys Thr Ala Lys
1

<210> SEQ ID NO 5
<211> LENGTH: 4
<212> TYPE: PRT
<213> ORGANISM: Artificial sequence
<220> FEATURE:
<223> OTHER INFORMATION: Synthetic peptide

<400> SEQUENCE: 5

Lys Ala Tyr Lys
1

<210> SEQ ID NO 6
<211> LENGTH: 4
<212> TYPE: PRT
<213> ORGANISM: Artificial sequence
<220> FEATURE:
<223> OTHER INFORMATION: Synthetic peptide

<400> SEQUENCE: 6

Lys Phe Tyr Lys
1

```
<210> SEQ ID NO 7
<211> LENGTH: 5
<212> TYPE: PRT
<213> ORGANISM: artificial sequence
<220> FEATURE:
<223> OTHER INFORMATION: synthetic peptide

<400> SEQUENCE: 7

Lys Thr Thr Lys Ser
1               5

<210> SEQ ID NO 8
<211> LENGTH: 6
<212> TYPE: PRT
<213> ORGANISM: artificial sequence
<220> FEATURE:
<223> OTHER INFORMATION: Synthetic peptide

<400> SEQUENCE: 8

Gly Lys Thr Thr Lys Ser
1               5

<210> SEQ ID NO 9
<211> LENGTH: 6
<212> TYPE: PRT
<213> ORGANISM: artificial sequence
<220> FEATURE:
<223> OTHER INFORMATION: synthetic peptide

<400> SEQUENCE: 9

Val Gly Val Ala Pro Gly
1               5

<210> SEQ ID NO 10
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 10

Gly Gln Pro Arg
1

<210> SEQ ID NO 11
<211> LENGTH: 4
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 11

Lys Thr Phe Lys
1

<210> SEQ ID NO 12
<211> LENGTH: 4
```

```
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 12

Lys Thr Phe Lys
1

<210> SEQ ID NO 13
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 13

Lys Thr Ala Lys
1

<210> SEQ ID NO 14
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 14

Lys Ala Tyr Lys
1

<210> SEQ ID NO 15
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 15

Lys Phe Tyr Lys
1

<210> SEQ ID NO 16
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
```

```
<223> OTHER INFORMATION: amidation by a Palmitoyl chain on the N
      terminal end

<400> SEQUENCE: 16

Lys Thr Thr Lys Ser
1               5

<210> SEQ ID NO 17
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (5)..(5)
<223> OTHER INFORMATION: Xaa being either a Proline P or a Leucine L.

<400> SEQUENCE: 17

Tyr Gly Gly Phe Xaa
1               5

<210> SEQ ID NO 18
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 18

Val Gly Val Ala Pro Gly
1               5

<210> SEQ ID NO 19
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 19

Gly Lys Thr Thr Lys Ser
1               5

<210> SEQ ID NO 20
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
<220> FEATURE:
```

```
<221> NAME/KEY: MISC_FEATURE
<222> LOCATION: (6)..(6)
<223> OTHER INFORMATION: Xaa being Trp, Phe, Tyr, Tic, 7-hydroxy-Tic or
      Tpi

<400> SEQUENCE: 20

His Leu Asp Ile Ile Xaa
1               5

<210> SEQ ID NO 21
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation on the N-terminal end

<400> SEQUENCE: 21

Glu Glu Met Gln Arg Arg
1               5

<210> SEQ ID NO 22
<211> LENGTH: 5
<212> TYPE: PRT
<213> ORGANISM: artificial sequence
<220> FEATURE:
<223> OTHER INFORMATION: synthetic peptide

<400> SEQUENCE: 22

Tyr Ala Gly Phe Leu
1               5

<210> SEQ ID NO 23
<211> LENGTH: 4
<212> TYPE: PRT
<213> ORGANISM: artificial sequence
<220> FEATURE:
<223> OTHER INFORMATION: synthetic peptide

<400> SEQUENCE: 23

Ala His Ser His
1

<210> SEQ ID NO 24
<211> LENGTH: 6
<212> TYPE: PRT
<213> ORGANISM: artificial sequence
<220> FEATURE:
<223> OTHER INFORMATION: synthetic peptide

<400> SEQUENCE: 24

Ser Ile Lys Val Ala Val
1               5

<210> SEQ ID NO 25
<211> LENGTH: 6
<212> TYPE: PRT
<213> ORGANISM: artificial sequence
<220> FEATURE:
<223> OTHER INFORMATION: synthetic peptide

<400> SEQUENCE: 25

Gly Pro Gln Gly Pro Gln
1               5
```